US007740837B2

(12) United States Patent
Fakhrai

(10) Patent No.: US 7,740,837 B2
(45) Date of Patent: *Jun. 22, 2010

(54) GENETICALLY MODIFIED CELLS EXPRESSING A TGF BETA INHIBITOR, THE CELLS BEING LUNG CANCER CELLS

(75) Inventor: Habib Fakhrai, La Jolla, CA (US)

(73) Assignee: Novarx, San Diego, CA (US)

(*) Notice: Subject to any disclaimer, the term of this patent is extended or adjusted under 35 U.S.C. 154(b) by 237 days.

This patent is subject to a terminal disclaimer.

(21) Appl. No.: 11/486,461

(22) Filed: Jul. 14, 2006

(65) Prior Publication Data

US 2007/0264242 A1 Nov. 15, 2007

Related U.S. Application Data

(63) Continuation of application No. 10/244,718, filed on Sep. 16, 2002, now Pat. No. 7,101,543, which is a continuation of application No. PCT/US01/10339, filed on Mar. 30, 2001.

(60) Provisional application No. 60/193,497, filed on Mar. 31, 2000.

(51) Int. Cl.
A61K 48/00 (2006.01)
A01N 63/00 (2006.01)
A01N 61/00 (2006.01)
C12N 15/00 (2006.01)
C12N 5/00 (2006.01)

(52) U.S. Cl. .................. 424/93.21; 424/93.1; 435/91.4; 435/320.1; 435/325

(58) Field of Classification Search ............... 424/93.21, 424/93.1; 435/91.4, 320.1, 325
See application file for complete search history.

(56) References Cited

U.S. PATENT DOCUMENTS

| 5,095,095 | A | 3/1992 | Fontana |
| 5,168,062 | A | 12/1992 | Stinski |
| 5,385,839 | A | 1/1995 | Stinski |
| 5,674,486 | A | 10/1997 | Sobol et al. |
| 5,681,562 | A | 10/1997 | Sobol et al. |
| 5,772,995 | A | 6/1998 | Fakhrai et al. |
| 5,824,655 | A | 10/1998 | Border |
| 6,120,763 | A | 9/2000 | Fakhrai et al. |
| 6,447,769 | B1 | 9/2002 | Fakhrai et al. |
| 6,455,689 | B1 | 9/2002 | Schlingensiepen et al. |
| 2002/0192199 | A1 | 12/2002 | Habib |
| 2003/0040499 | A1 | 2/2003 | Sclingensiepen et al. |
| 2003/0050265 | A1 | 3/2003 | Dean et al. |
| 2004/0006030 | A1 | 1/2004 | Monia |
| 2004/0063655 | A1 | 4/2004 | Dean et al. |
| 2004/0147472 | A1 | 7/2004 | Murray et al. |

FOREIGN PATENT DOCUMENTS

| EP | 0695 354 B1 | 1/2002 |
| WO | WO 85/04421 | 10/1985 |
| WO | WO 88/03807 | 6/1988 |
| WO | WO 93/07906 A1 | 4/1993 |
| WO | WO 94/25588 A2 | 11/1994 |
| WO | WO 96/02143 A1 | 2/1996 |
| WO | WO 96/25178 A1 | 8/1996 |
| WO | WO 97/27876 | 8/1997 |
| WO | WO 01/19161 | 3/2001 |
| WO | WO 01/74404 A2 | 10/2001 |
| WO | WO 2004/005552 | 1/2004 |
| WO | WO 2005/084712 | 9/2005 |

OTHER PUBLICATIONS

Gold L. Critical Reviews in Ontogenesis, 1999, The role of transforming Growth Factor Beta (TGF), pp. 303-360.*
Voskoglou-Nomikos T,et al., Clinical predictive value of the in vitro cell line, human xenograft, and mouse allograft preclinical cancer models.Clin Cancer Res. Sep. 15, 2003;9(11):4227-39.*
KoheiMiyazono et al., TGF-β signaling by Smad proteins Cytokine & Growth Factor Reviews vol. 11, Issues 1-2, Apr. 2000, pp. 15-22.*
Chen et al., Microsatellite alterations in plasma DNA of small cell lung cancer patients Nat Med. Sep. 1996;2(9):1033-5.*
Fisher et al., 1994, Eur. J. Cancer (1994) 30A:2125-2129.*
Asselin-Paturel, C. et al. 1998 "Quantitative analysis of Th1, Th2 and TGF-β1 cytokine expression in tumor, Til and PBL of non-small cell lung cancer patients." *Int. J. Cancer* 77: 7-12.
Fakhrai H. et al. 1996 "Eradication of established intracranial rat gliomas by transforming growth factor β antisense gene therapy." *PNAS USA* 93: 2909.
Fakhrai, H. et al. 2000 "Gene therapy of human gliomas with TGF-β2 antisense gene modified autologous tumor cells. A Phase I clinical trial." *Proc. Amer. Assoc. Cancer Res. Annu. Meeting* 41:543.
Fakhrai, H. et al., 1995 "Immunization with TGF-β2 antisense gene modified tumor cells eradicates intracranial gliomas." *Proc. Annu. Meeting of the Amer. Assoc. Cancer Res.* 36:463-E.
Fischer, J.R., et al. 1994 "Constitutive secretion of bioactive transforming growth factor $β_1$ by small cell lung cancer cell lines." *Eur. J. Cancer* 30A:2125-2129.
Goodman and Gilman's 1996 "*The Pharmacological Basis of Therapeutics*" Ninth Edition, McGraw-Hill, pp. 77-101.
Marshall, E. 1995 "Gene therapy's growing pains." *Science* 269: 1050-1055.
Norgaard, P. et al. 1996 "Expression and autoregulation of transforming growth factor β receptor mRNA in small-cell lung cancer cell lines." *Brit. J. Cancer* 73:1037-1043.
Ogawa, Y. et al. 1991 "Purification of transforming growth factors $β1$ and $β2$ from bovine bone and cell culture assays." *Meth. Enzymol.* 198: 317-327.
Report and Recommendations of the Panel to Assess the NIH Investment in Research on Gene Therapy, Dec. 1995, p. 11.

(Continued)

Primary Examiner—Maria Leavitt
(74) Attorney, Agent, or Firm—Morrison & Foerster LLP

(57) ABSTRACT

The present invention relates to compositions comprising a therapeutically effective amount of genetically modified cells containing a genetic construct expressing a TGFβ inhibitor effective to reduce expression of TGFβ, where the genetically modified cells are non-small cell lung cancer (NSCLC) cells or small cell lung cancer (SCLC) cells, and related methods.

16 Claims, No Drawings

OTHER PUBLICATIONS

Sandhu, J.S. et al. 1997 "Human gene therapy." *Crit. Rev. Biotechnol.* 17:307-326.

Schwartzentruber, D.J. et al. 1993 "Tumor-infiltrating lymphocytes derived from select B-cell lymphomas secrete granulocyte-macrophage colony-stimulating factor and tumor necrosis factor-$\alpha$ in response to autologous tumor stimulation." *Blood* 82:1204-1211.

Sharma, S. et al. 1997 "Multicomponent gene therapy vaccines for lung cancer: effective eradication of established murine tumors in vivo with interleukin-7/herpes simplex thymidine kinase-transduced autologous tumor and ex vivo activated dendritic cells." *Gene Ther.* 4:1361-1370.

Sobol, R.E. et al. 1999 "Interleukin 2 gene therapy of colorectal carcinoma with autologous irradiated tumor cells and genetically engineered fibroblasts: a Phase I study." *Clin. Cancer. Res.* 5:2359-2365.

\* cited by examiner

GENETICALLY MODIFIED CELLS EXPRESSING A TGF BETA INHIBITOR, THE CELLS BEING LUNG CANCER CELLS

CROSS-REFERENCE TO RELATED APPLICATIONS

This application is a continuation of U.S. application Ser. No. 10/244,718, filed Sep. 16, 2002, now U.S. Pat. No. 7,101, 543 which is a continuation of International Application No. PCT/US01/10339, filed Mar. 30, 2001, designating the United States of America and published in English, which claims the benefit of priority of U.S. provisional patent application No. 60/193,497, filed Mar. 31, 2000, all of which are hereby expressly incorporated by reference in their entireties.

BACKGROUND OF THE INVENTION

1. Field of the Invention

The present invention relates to compositions comprising a therapeutically effective amount of genetically modified cells containing a genetic construct expressing a TGFβ inhibitor effective to reduce expression of TGFβ, where the genetically modified cells are non-small cell lung cancer (NSCLC) or small cell lung cancer (SCLC) cells, and related methods.

2. Description of the Related Art

Lung cancer remains the most prevalent cancer in the western world, accounting for 30% of all cancer-related deaths (Ramanathan and Belani, 1997). The current prognosis for patients with lung cancer is poor. The overall cure rate is estimated as low as 13%. Approximately 180,000 new cases of lung cancer are expected in the United States in 1999. The majority of these patients will die of their disease with 160,000 deaths from lung cancer expected nation-wide in 1999.

There are two major subdivisions of lung cancer: 1) non-small cell (NSCLC) and 2) small cell lung cancer (SCLC). Treatment approaches and natural history differ for these two diseases. The majority (80%) of cases of lung cancer in the United States are NSCLC. Although advances in the understanding of important clinical and prognostic factors for both NSCLC and SCLC have been made in the past 20 years, there have been minimal improvements in therapeutic results. The only curative option for patients with NSCLC is local therapy (surgical excision or local irradiation) in patients with early stage disease (I & II) when the tumor is still localized. At diagnosis however, the majority of patients with NSCLC present with advanced disease, which is not curable by surgery alone. In advanced stages of disease, systemic chemotherapy and/or irradiation can produce objective responses and palliation of symptoms, however, they offer only modest improvements in survival. The median survival of patients with non-resectable disease is 6-12 months. Two-year survival rates for stages IIIB and IV NSCLC are 10.8 and 5.4 percent respectively. Likewise, five-year survival rates are 3.9 and 1.3 percent. Recently, several new drugs have become available for the treatment of NSCLC including paclitaxel (Taxol), docetaxel (Taxotere), topotecan, irinotecan, vinorelbine, and gemcitabine. While these drugs are improvements over prior chemotherapeutic agents (etoposide, cisplatin and carboplatin), the overall cure rate remains low.

SCLC is a very aggressive cancer which metastasizes early and often, and it has a median survival from diagnosis of only two to four months. Localized forms of treatment, such as surgical resection or radiation therapy, rarely produce long-term survival because of this cancer's propensity for distant metastasis. With chemotherapy, survival can be prolonged at least four to five times the media survival rate for patients who are given no therapy, however the overall survival at five years remains at only 5-10%.

Since current therapeutic modalities do not significantly enhance life expectancy in stages of NSCLC or SCLC patients, exploration of new therapeutic approaches for these patients is justified.

SUMMARY OF THE INVENTION

Patients bearing tumors of different histologic origin have elevated levels of Transforming Growth Factors-βs (TGFβs). TGFβs are growth factors that are associated with immunosuppression. Suppression of the patients' immune system results in their inability to recognize and destroy tumors when they first appear. Furthermore, suppression of patients' immunity makes them susceptible to frequent infections. Injection of genetically engineered tumor cells to block their TGFβ production makes the gene modified cells potent vaccines that are recognized by and can activate the immune system against the tumor. Activation of the immune system subsequently causes the recognition and control of the parental unmodified tumors in the host organisms. This phenomenon applies in animal tumor models and in human clinical trials. Thus, we propose to use this approach in patients with stages of non-small cell lung and small cell lung cancers.

DETAILED DESCRIPTION OF THE PREFERRED EMBODIMENT

Lung cancers account for 30% of all death due to cancer in the United States (Ramanathan and Belani, 1997). The overall cure rate for lung cancer is 13% and the current prognosis for patients with non-small cell lung (NSCLC) and small cell lung cancer (SCLC) remains poor.

It has been documented that patients with progressive tumor growth have impaired immune function (Jakowlew et al. 1995, Ransohoff et al 1991; Holladay et al. 1992a; Holladay et al. 1992b). This impairment, commonly characterized as marked immune hyporesponsiveness, is not solely confined to tumor specific immunity, but rather, is often observed throughout the immune system. Impairment is especially evident in the cell-mediated or T-cell compartment and is characterized by T-cell lymphopenia and impaired T-cell responsiveness to both tumor specific and non-tumor specific stimuli (Ransohoff et al. 1991). One way tumors may escape immune surveillance is by expressing lower levels of MHC Class I and Class II molecules. Other tumors may escape by increasing the expression of immunosuppressor molecules, such as the TGFβs. It is common to observe tumors utilizing a combination of these mechanisms.

Gene therapy has received considerable attention in recent years. Vaccination with tumor cells designed to augment tumor antigen presentation and induce specific anti-tumor immunity has yielded promising but limited results (Holladay et al. 1992). Advances in our understanding of cancer biology and developments in vector technologies are advancing the therapeutic potential of tumor vaccine approaches. It is now possible to genetically modify tumor cells for vaccination to express specific tumor suppressor genes, immune modulators, drug sensitive genes and antisense gene fragments (Huber et al. 1991; Culver et al. 1992; Trojan et al. 1992; Dranoff et al. 1993; Ram et al. 1993; Trojan et al. 1993; Swisher et al. 1999). In particular preclinical and clinical studies demonstrate the potential of gene therapy approaches in treating lung cancer. Preclinical lung cancer models have shown regression of established tumors and enhanced immunogenicity using an allogeneic lung cancer line genetically modified to express the cytokine GM-CSF and a drug sensitive gene, herpes simplex virus thymidine kinase admixed with syngeneic bone-marrow derived dendritic cells (Miller et al. 1998). Preliminary results from phase I clinical trials in patients using retroviral gene therapy shows gene therapy to be well tolerated and without toxicity (Swisher et al. 1998).

Transforming growth factors beta (TGFβ) are a family of multi-functional proteins that regulate the growth and function of many normal and neoplastic cell types (Sporn et al. 1986; Massague 1987; Border and Rouslahti 1992; Jachimczak et al. 1993). They exert a wide range of effects on a variety of cell types and have been shown to stimulate or inhibit cell growth, induce apoptosis and increase angiogenesis (Merzak et al. 1994; Jennings et al. 1994; Ashley et al. 1998a; Ashley et al. 1998b; Jennings et al. 1998). These effects are mediated at the level of signal transduction. TGFβ signal transduction has been found to affect the expression of more than 20 different genes (Baker and Harland 1997; Heldin et al. 1997; Stiles 1997; Yingling et al; 1997).

TGFβ exists in three isoforms, known as TGFβ 1, TGFβ 2, and TGFβ 3. Their amino acid sequences display homologies on the order of 70-80%. Human TGFβ proteins and genes encoding them are known in the art. Specifically, TGFβ 1 mRNA (GenBank Accession No. XM_008912 and NM_000660), TGFβ 2 mRNA (GenBank Accession No. XM_001754 and NM_003238), and TGFβ 3 mRNA (GenBank Accession No. XM_007417) from human sources have been documented.

TGFβ receptor proteins may be type I (55 kDa) or type II (70 kDa). TGFβ receptor proteins and genes encoding them are also known in the art. Human TGFβ receptor type I mRNA (GenBank Accession No. XM_005591) and human TGFβ receptor type II mRNA (GenBank Accession No. XM_003094) are described in the art.

Cytokines of the TGFβ superfamily bind to specific serine/threonine kinase receptors and transmit intracellular signals through Smad proteins. Upon ligand stimulation, Smads move into the nucleus and function as components of transcription complexes. TGFβ signaling is regulated positively and negatively though various mechanisms. Positive regulation amplifies signals to a level sufficient for biological activity. Negative regulation occurs at the extracellular, membrane, cytoplasmic and nuclear levels.

Many tumors, including NSCLC and SCLC, produce high levels of active TGFβ (Constam et al. 1992; Eastham et al. 1995; Friedman et al. 1995; Jakowlew et al. 1995; Kong et al. 1995; Yamada et al. 1995; Eder et al. 1996). Elevated TGFβ levels have also been linked with immunosuppression (Sporn et al. 1986; Massague 1987; Bodmer et al. 1989; Border and Rouslahti 1992; Chen et al. 1997). TGFβ inhibits T cell activation in response to antigen stimulation. Additionally, TGFβ has antagonistic effects on the Natural Killer (NK) cells as well as the induction and proliferation of the lymphokine-activated killer (LAK) cells (Rook et al. 1986; Kasid et al. 1988; Tsunawaki et al. 1988; Hirte et al. 1991; Ruffini et al. 1993; Naganuma et al. 1996). In support of this, a relationship between TGFβ levels and survival has been demonstrated in colon cancer (Friedman et al. 1995). Recurrence rates were 18 fold higher in patients whose tumor produced high levels of TGFβ compared to those whose tumor produced low levels. This relationship was independent of nodal status and the degree of differentiation of the primary tumor.

Given the role of TGFβ in immune suppression we set out to evaluate the effect of TGFβ inhibition by NSCLC tumor vaccination. Using a TGFβ inhibitor approach we transfected a number of NSCLC cells with TGFβ antisense, selected from TGFβ1, TGFβ2, and TGFβ3, and mixtures thereof. TGFβ2 antisense was chosen as it demonstrated superiority in downregulating TGF TGFβ expression compared with TGF TGFβ1 or a combination of TGF TGFβ1 and TGF TGFβ2. These genetically modified NSCLC cells were then irradiated to prevent proliferation and were injected into a number of different animal tumor subjects. We observed that NSCLC cells previously ineffective as a component of a vaccine could be rendered efficacious through such a genetic modification. Blocking TGFβ expression increased the immunogenicity of these animals. Furthermore such vaccinations eradicated previously implanted tumors and protected animals from tumor challenge.

Given the role of TGFβ in immune suppression we envision evaluating the effect of TGFβ inhibition by SCLC tumor vaccination. Using a TGFβ inhibitor approach we envision transfecting a number of SCLC cells with TGFβ antisense, selected from TGFβ1, TGFβ2, and TGFβ3, and mixtures thereof. These genetically modified SCLC cells are then irradiated to prevent proliferation and are injected into a number of different animal tumor subjects. We envision observing that SCLC cells previously ineffective as a component of a vaccine would be rendered efficacious through such a genetic modification. Blocking TGFβ expression is envisioned as increasing the immunogenicity of these animals. Furthermore such vaccinations are envisioned as eradicating previously implanted tumors and protecting animals from tumor challenge.

We have shown the efficacy of this approach in a NSCLC tumor model. In the KLN-205 NSCLC tumor model, DB2 mice were vaccinated with two injections of $5 \times 10^5$ irradiated TGFβ2 antisense gene modified autologous NSCLC cells. This was capable of protecting the animals against a subsequent intraperitoneal (i.p.) tumor challenge with $10^6$ unmodified KLN-205 NSCLC cells. In eradication experiments in this lung cancer tumor model, vaccination of animals bearing one week old tumors, with TGFβ2 antisense gene modified cells resulted in marked tumor regression and prolonged tumor free survival compared to the control group.

Fakhrai et al. 1996 demonstrated the efficacy of this approach in a rat glial tumor. In the 9 L gliosarcoma tumor model, intracranial implantation of as few as 300 tumor cells in Fisher-344 rat resulted in over 99% fatality after six weeks. Fakhrai et al. 1996 implanted $5 \times 10^3$ tumor cells into the brain of rats and administered tumor vaccinations. Animals immunized with TGFβ2 antisense modified 9 L cells, or with TGFβ2 antisense modified 9 L cells genetically modified to secrete IL-2 remained tumor free for the duration of the study (24 out of 24 or 100% tumor free survival). In contrast, the majority of the control group (2 out of 15) immunized with cells containing the empty vector developed tumors and had to be euthanized within five weeks (13% tumor free survival, $p<0.01$).

Liau et al. 1998 demonstrated comparable efficacy of TGFβ2 antisense gene therapy in a rat C-6 glioma tumor model. Dorigo et al. 1998 showed the efficacy of this approach in a murine ovarian teratoma (MOT) tumor model; however, only the group inoculated with TGFβ antisense and IL-2 gene modified cells resulted in significant protection from a subsequent tumor challenge, thus establishing the empiricism of the approach. Other groups have demonstrated similar anti-tumor effects of TGFβ gene therapy in cultured cells and animal tumor models (Kim et al. 1997).

Gene therapy has received considerable attention in recent years. Vaccination with tumor cells designed to augment tumor antigen presentation and induce specific anti-tumor immunity has yielded promising but limited results.

Advances in our understanding of cancer biology and developments in vector technologies are advancing the therapeutic potential of tumor vaccination. It is now possible to genetically modify tumor cells for vaccination to express specific tumor suppressor genes, immune modulators, drug sensitive genes or antisense gene fragments (Huber et al. 1991; Culver et al. 1992; Trojan et al. 1992; Dranoff et al. 1993; Ram et al. 1993; Trojan et al. 1993).

A number of clinical studies have evaluated genetically modified allogeneic tumor cell as primary components of immunotherapeutic treatments for brain, skin, colon and breast cancers. The vaccination regimens have been shown to be safe and to generate humoral and cellular anti-vaccine immune responses. Preliminary results from several phase I clinical trials using gene therapies in patients with NSCLC have also demonstrated the safety of gene therapies approaches for this patient population (Dubinett, 1998; Roth, 1998; Swisher et al. 1998) as well as a SCLC patient population.

Groups have demonstrated experience in the field of gene therapy, both in a number of animal tumor models and in the clinic. (E.g., Fakhrai et al. 1995; Sobol et al. 1999.) The FDA has previously approved at least four INDs that have been submitted investigating gene-modified vaccination in patients with cancer:

Sobol et al., BB-IND # 5812: "Injection of colon carcinoma patients with autologous irradiated tumor cells and fibroblasts genetically modified to secrete interleukin-2 (IL-2). A Phase I study"

Sobol et al., BB-IND # 4840: "Active immunotherapy of glioblastoma with tumor cells or fibroblast genetically modified to secrete interleukin-2 (IL-2)"

Sobol et al., BB-IND # 7483: "A Phase I Study of Allogeneic Tumor Cells Genetically Modified t Express B7.1 (CD80) Mixed with Allogeneic Fibroblasts Genetically Modified to Secrete IL-2 in Patients with Colorectal Carcinoma"

Fakhrai et al. BB-IND # 6658: "Proposal for a Phase I Clinical Trial: A Phase I Study of the Safety o Injecting Malignant Glioma Patients with Irradiated TGFβ2 Antisense Gene-Modified Autologous Tumor Cells"

In BB-IND #6658, the FDA approved a Phase I IND evaluating TGFβ2 antisense gene therapy in patients with high grade glioma. Patients were vaccinated with autologous glioma tumor cells genetically modified with a TGFβ2 antisense plasmid to block TGFβ2 expression. Therapy consisted of intradermal injections with $5 \times 10^6$, $1 \times 10^7$ or $2 \times 10^7$ cells every 3 weeks for the first 4 months and every 1-2 months thereafter. To date, 5 patients have been treated. Under the same IND, the FDA approved the compassionate use of a partially haplotype matched allogeneic glioma cell line which was gene modified with the same TGFβ2 antisense vector in a patient with pediatric glioma.

Overall treatment has been well tolerated with only low grade, transient toxicities reported. No significant adverse reactions at the immunization sites and no treatment-related abnormalities have been observed on monitoring of complete blood counts, serum chemistries and urinalyses. In a few cases transient, mild erythema has been observed at the injection sites following the second and third subcutaneous injections with TGFβ2 antisense gene-modified autologous tumor cells.

Increased levels of CD3+, CD4+ and CD8+ effector cell infiltrates at the injection site and in secondary tumor biopsies have been observed. Immune histology of injection site biopsies and tumor obtained at subsequent operation demonstrates significantly higher number of immune infiltrates in comparison to biopsies taken prior to initiation of gene therapy.

Of the 5 patients treated, 1 patient demonstrated a clinical response, 2 demonstrated enhanced immune response, 1 showed tumor progression while the fifth patient is still undergoing therapy. In the patient who had a clinical response, overall MRI scans performed at approximately 6-week intervals during the first three months of treatment revealed modest changes in overall tumor size. Waxing and waning of peri-tumoral edema associated with alterations in Decadron doses could be observed. However, MRI scans showed tumor regression by seven months with a further improvement in response 3 months later.

The phase I clinical trial thus demonstrated the safety of injecting patients with $5 \times 10^6$, $1 \times 10^7$ or $2 \times 10^7$ of TGFβ2 antisense gene-modified autologous or haplotype-matched tumor cells. Furthermore, it is encouraging to see enhanced immunogenicity and preliminary clinical responses seen with this vaccination regimen. We contemplate the application of this gene therapy approach in patients with NSCLC or SCLC.

The invention encompasses methods and compositions for prolonging the survival of a subject having a non-small cell lung cancer (NSCLC) or a small cell lung cancer (SCLC) comprising administering to the subject a therapeutically effective amount of genetically modified cells containing a genetic construct expressing a TGFβ inhibitor effective to reduce expression of TGFβ, where the genetically modified cells are NSCLC or SCLC cells. Any method which neutralizes TGFβ or inhibits expression of the TGFβ gene (either transcription or translation) can be used to effectuate subject survival. Such approaches can also be useful for treatment applications, i.e., to treat NSCLC or SCLC.

In one embodiment, survival modalities can be designed to reduce the level of endogenous TGFβ gene expression, e.g., using antisense or ribozyme approaches to reduce or inhibit translation of TGFβ mRNA transcripts; triple helix approaches to inhibit transcription of the TGFβ gene; or targeted homologous recombination to inactivate or "knock out" the TGFβ gene or its endogenous promoter.

Antisense approaches involve the design of oligonucleotides (either DNA or RNA) that are complementary to TGFβ mRNA. The antisense oligonucleotides will bind to the complementary TGFβ mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-335. Thus, oligonucleotides complementary to either the 5'- or 3'-non-translated, non-coding regions of TGFβ could be used in an antisense approach to inhibit translation of endogenous TGFβ mRNA. Oligonucleotides complementary to the 5' untranslated region of the mRNA should include the complement of the AUG start codon. Antisense oligonucleotides complementary to mRNA coding regions could also be used in accordance with the invention. Whether designed to hybridize to the 5'-, 3'- or coding region of TGFβ mRNA, antisense nucleic acids should be at least six nucleotides in length, and are preferably oligonucleotides ranging from 6 to about 50 nucleotides in length. In specific aspects the oligonucleotide is at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al. 1989 *PNAS USA* 86:6553-6556; Lemaitre et al. 1987 *PNAS USA* 84:648-652; PCT Publication No. WO88/09810, published Dec. 15, 1988).

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopente-nyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988 *Nucl. Acids Res.* 16:3209), methylphosphonate oligonucleotides can be prepared by use of controlled pore glass polymer supports (Sarin et al. 1988 *PNAS USA* 85:7448-7451), etc.

However, it is often difficult to achieve intracellular concentrations of the antisense sufficient to suppress translation of endogenous mRNAs. Therefore a convenient approach utilizes a recombinant DNA construct in which the antisense sequence is placed under the control of a strong promoter. The use of such a construct to transfect target cells will result in the transcription of sufficient amounts of single stranded RNAs that will form complementary base pairs with the endogenous TGFβ transcripts and thereby prevent translation of the TGFβ mRNA. For example, a vector can be introduced such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bemoist and Chambon 1981 *Nature* 290:304-310), the promoter contained in the 3' long terminal repeat of Rous sarcoma virus (Yamamoto et al. 1980 *Cell* 22:787-797), the herpes thymidine kinase promoter (Wagner et al. 1981 *PNAS USA* 78:1441-1445), the regulatory sequences of the metallothionein gene (Brinster et al. 1982 *Nature* 296:39-42), etc.

Ribozyme molecules-designed to catalytically cleave TGFβ mRNA transcripts can also be used to prevent translation of TGFβ mRNA and expression of TGFβ. (See, e.g., PCT International Publication WO90/11364, published Oct. 4, 1990; Sarver et al. 1990 *Science* 247:1222-1225). While ribozymes that cleave mRNA at site specific recognition sequences can be used to destroy TGFβ mRNAs, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art and is described more fully in Haseloff and Gerlach 1988 *Nature* 334:585-591. There are hundreds of potential hammerhead ribozyme cleavage sites within the nucleotide sequence of a TGFβ cDNA. Preferably the ribozyme is engineered so that the cleavage recognition site is located near the 5' end of the TGFβ mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena Thermophila* (known as the IVS, or L-19 IVS RNA) and which has been extensively described by Thomas Cech and collaborators (Zaug, et al. 1984 *Science* 224:574-578; Zaug and Cech 1986 *Science* 231:470-475; Zaug, et al. 1986 *Nature* 324:429-433; published International patent-application No. WO 88/04300 by University Patents Inc.; Been and Cech 1986 *Cell* 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in TGFβ.

As in the antisense approach, the ribozymes can be composed of modified oligonucleotides (e.g., for improved stability, targeting, etc.) and need be delivered to target cells which express TGFβ. A convenient method of delivery involves using a DNA construct encoding the ribozyme under the control of a strong promoter so that transfected cells will produce sufficient quantities of the ribozyme to destroy endogenous TGFβ messages and inhibit translation. Because ribozymes unlike antisense molecules, are catalytic, a lower intracellular concentration is required for efficiency.

Endogenous TGFβ gene expression can also be reduced by inactivating or "knocking out" the TGFβ gene or its promoter using targeted homologous recombination. (E.g., see Smithies et al. 1985 *Nature* 317:230-234; Thomas & Capecchi 1987 *Cell* 51:503-512; Thompson et al. 1989 *Cell* 5:313-321). For example, a mutant, non-functional TGFβ (or a completely unrelated DNA sequence) flanked by DNA homologous to the endogenous TGFβ gene (either the coding regions or regulatory regions of the TGFβ gene) can be used, with or without a selectable marker and/or a negative selectable marker, to transfect target cells that express TGFβ. Insertion of the DNA construct, via targeted homologous recombination, results in inactivation of the TGFβ gene.

Alternatively, endogenous TGFβ gene expression can be reduced by targeting deoxyribonucleotide sequences complementary to the regulatory region of the TGFβ gene (i.e., the TGFβ promoter and/or enhancers) to form triple helical structures that prevent transcription of the TGFβ gene in target cells. (See generally, Helene, C. 1991 *Anticancer Drug Des.* 6(6):569-84; Helene, C. et al. 1992 *Ann. N.Y. Acad. Sci.* 660:27-36; and Maher, L. J. 1992 *Bioassays* 14(12):807-15).

In yet another embodiment of the invention, the activity of TGFβ can be reduced using a "dominant negative" approach to effectuate subject survival. To this end, genetic constructs which encode defective TGFβs can be used to diminish the activity of TGFβ on neighboring cells. For example, nucleotide sequences that direct expression of TGFβs in which domains are deleted or mutated can be introduced into target cells. Alternatively, targeted homologous recombination can be utilized to introduce such deletions or mutations into the target cell's endogenous TGFβ gene. The engineered cells will express non-functional cytokines (i.e., a cytokine that is capable of binding its natural receptor, but incapable of signal transduction). Such engineered cells should facilitate a diminished response on neighboring cells to endogenous TGFβ ligand, resulting in subject survival.

In an alternative embodiment, the administration of genetic constructs encoding soluble peptides, proteins, fusion proteins, or antibodies that bind to and "neutralize" intracellular TGFβ effectuate subject survival. To this end, genetic constructs encoding peptides corresponding to domains of the TGFβ receptor, deletion mutants of the TGFβ receptor, or either of these TGFβ receptor domains or mutants fused to another polypeptide (e.g., an IgFc polypeptide) can be utilized. Alternatively, genetic constructs encoding anti-idiotypic antibodies or Fab fragments of antiidiotypic antibodies that mimic the TGFβ receptor and neutralize TGFβ can be used. Such genetic constructs encoding these TGFβ receptor peptides, proteins, fusion proteins, anti-idiotypic antibodies or Fabs are administered to neutralize TGFβ and effectuate subject survival.

Genetic constructs encoding antibodies that specifically recognize one or more epitopes of TGFβ, or epitopes of conserved variants of TGFβ, or peptide fragments of TGFβ are also encompassed by the invention. Such antibodies include but are not limited to polyclonal antibodies, monoclonal antibodies (mAbs), humanized or chimeric antibodies, single chain antibodies, Fab fragments, F(ab')2 fragments, fragments produced by a Fab expression library, and epitope-binding fragments of any of the above. Genetic constructs encoding such antibodies may be used as a method for the inhibition of TGFβ activity and effectuation of subject survival.

For the production of antibodies, various host animals may be immunized by injection with TGFβ, a TGFβ peptide, truncated TGFβ, functional equivalents of TGFβ or mutants of TGFβ. Such host animals may include but are not limited to rabbits, mice, and rats, to name but a few. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975 *Nature* 256:495-497; and U.S. Pat. No. 4,376,110), the human B-cell hybridoma technique (Kosbor et al. 1983 *Immunology Today* 4:72; Cole et al. 1983 *PNAS USA* 80:2026-2030), and the EBV-hybridoma technique (Cole et al. 1985 *Monoclonal Antibodies And Cancer Therapy*, Alan R. Liss, Inc., pp. 77-96). Such antibodies may be of any immunoglobulin class including IgG, IgM, IgE, IgA, IgD and any subclass thereof.

In addition, techniques developed for the production of "chimeric antibodies" (Morrison et al. 1984 *PNAS USA* 81:6851-6855; Neuberger et al. 1984 *Nature* 312:604-608; Takeda et al. 1985 *Nature* 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988 *Science* 242:423-426; Huston et al. 1988 *PNAS USA* 85:5879-5883; and Ward et al. 1989 *Nature* 334:544-546) can be adapted to produce single chain antibodies against TGFβ gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, Fab expression libraries may be constructed (Huse et al. 1989 *Science* 246:1275-1281) to allow rapid and easy identification of monoclonal Fab fragments with the desired specificity.

Additionally, the enzymes which cleave TGFβ precursors to the active isoforms may be inhibited in order to block activation of TGFβ. TGFβ must be activated to exhibit its biological effects and enzymes are required to cleave the precursor protein. These enzymes may be altered genetically to prevent interaction with the precursor protein, preventing cleavage of the protein to its mature form. Transcription or translation of these enzymes may be blocked by a means known to the art. These enzymes may alternatively be inhibited by any means known to one of skill in the art.

TGFβs bind to serine/threonine kinase receptors and transmit intracellular signals through Smad proteins. Signal transduction may be interrupted in order to repress signaling initiated by TGFβ. By disrupting signal transduction it is possible to prevent the immunosuppressive effect of TGFβ. This may be accomplished by any means known in the art in which the interaction between the TGFβ receptor and the Smad protein is antagonized or prevented, including administering genetically modified cells which express proteins that block or compete with TGFβ receptor and Smad protein interactions. Alternatively, the transcription or translation of TGFβ receptor or Smad protein may be altered by any means known in the art in order to prevent signal transmission along the signaling pathway.

Target cells genetically engineered to express such a form of TGFβ inhibitor are administered as an immunogen to patients with NSCLC or SCLC, whereupon they will serve to enhance anti-tumor immune responses and thereby prolong survival of tumor-bearing subjects. Such cells may be obtained from the patient (autologous) or a donor (allogeneic or xenogeneic). For a patient with NSCLC, the genetically engineered cells constitute non-small cell lung cancer (NSCLC) cells, which are NSCLC cells by virtue of being derived from a NSCLC or mimicking a NSCLC (i.e., having shared common tumor antigens or epitopes with a primary NSCLC). Alternatively, for a patient with SCLC, the genetically engineered cells constitute small cell lung cancer (SCLC) cells, which are SCLC cells by virtue of being derived from a SCLC or mimicking a SCLC (i.e., having shared common tumor antigens or epitopes with a primary SCLC).

Autologous cells are cell that are derived from the same individual. Allogeneic cells are cells that are derived from another individual of the same species so that the cells have intraspecies genetic variations. Xenogeneic cells are cells that are derived from an individual of a different species so that the cells have interspecies antigenic differences.

In one embodiment, an allogeneic (or xenogeneic) NSCLC or SCLC tumor cell line is chosen as the immunogen. Lung tumor cell lines have been shown to have shared epitopes with primary tumors (Takenoyama et al. 1998). These investigators showed that MHC class I restricted CTL generated against a human lung adenocarcinoma cell line had demonstrable cytotoxicity against another lung tumor cell line. The cross reactivity in these experiments was blocked by anti-MHC class I and anti-CD8 monoclonal antibodies, suggesting that shared common tumor antigens exist among lung cancer cells.

In another embodiment, an allogeneic (or xenogeneic) cell cocktail is used as an immunogen in patients with NSCLC or SCLC. One can employ more than one, e.g., two, three, four or more cell lines rather than one to increase the total number of tumor antigens present.

In addition, the target cells will have low levels of TGFβ expression owing to transfection with a genetic construct encoding a TGFβ2 inhibitor. Suppression of TGFβ expression by the tumor cells will remove a major source of immune suppression operative at the site of vaccine injection. A local immune response, directed against the injected tumor cells will induce a systemic immune response against the patients' native tumor.

The target cells are genetically engineered in vitro using recombinant DNA techniques to introduce the genetic constructs into the cells, e.g., by transduction (using viral vectors) or transfection procedures, including but not limited to the use of plasmids, cosmids, YACs, electroporation, liposomes, etc. The engineered cells can be introduced into the patient, e.g., in the circulation, intraperitoneally, intradermally, subcutaneously, at the lobes of the lung. Alternatively, the cells can be incorporated into a matrix and implanted in the body as part of a tissue graft.

In another embodiment, target cells are engineered to express a coding sequence for one or more cytokines. In one alternative, an expression vector singly encoding the one or more cytokines is introduced into the target cells. In another alternative, an expression vector doubly encoding the one or more cytokines and a TGFβ inhibitor is introduced into the target cells. In still another alternative, some target cells are engineered to express a coding sequence for one or more cytokines and other target cells are genetically modified to express a TGFβ inhibitor. By co-administering the immunostimulatory agent along with inhibiting the immunosuppressant TGFβ, a subject's immune response to tumor cells may be improved. Examples of cytokines useful for practice of the present invention include interleukin-1, interleukin-2, interleukin-3, interleukin-4, interleukin-5, interleukin-6, interleukin-7, interleukin-8, interleukin-9, interleukin-10, interleukin-11, interleukin-12, interleukin-15, interferon-alpha, interferon-gamma, tumor necrosis factor-alpha, transforming growth factor-beta, granulocyte macrophage colony stimulating factor, and granulocyte colony stimulating factor. The level of cytokine expression should be regulated such that anti-tumor immunity can be increased without producing significant systemic toxicity in the subject.

When the target cells to be administered are non-autologous cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Toxicity and therapeutic efficacy of NSCLC or SCLC cells can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Numbers of NSCLC or SCLC cells which exhibit large therapeutic indices are preferred.

The data obtained from the cell culture assays and animal studies can be used in formulating a range of dosage for use in humans. The dosage for humans lies preferably within a range of concentrations that include the $ED_{50}$ with little or no toxicity. For any number of NSCLC or SCLC cells used in the invention, the therapeutically effective dose can be estimated initially from cell culture assays. A dose may be formulated in animal models to achieve a concentration range that includes the $IC_{50}$ (i.e., the concentration of the test material which achieves a half-maximal inhibition of symptoms) as determined in cell culture. Such information can be used to more accurately determine useful doses in humans.

Pharmaceutical compositions for use in accordance with the present invention may be formulated in a conventional manner using one or more physiologically acceptable carriers or excipients. Various adjuvants may be used to increase the immunological response, including QS-21, Detox-PC, MPL-SE, MoGM-CSF, TiterMax-G, CRL-1005, GERBU, TERamide, PSC97B, Adjumer, PG-026, GSK-1, GcMAF, B-alethine, MPC-026, Adjuvax, CpG ODN, Betafectin, Alum, and MF59 (see Kim et al. 2000 *Vaccine* 18: 597 and references therein). Formulations for injections may be presented in unit dosage form, e.g., in ampoules or multi-dose containers.

The present invention further provides a therapeutic composition comprising the genetically modified cells expressing a TGFβ inhibitor and a therapeutically acceptable carrier. As used herein, a therapeutically acceptable carrier includes any and all solvents, including water, dispersion media, culture from cell media, isotonic agents and the like that are non-toxic to the host. Conveniently, it is an aqueous isotonic buffered solution with a pH of around 7.0. The use of such media and agents in therapeutic compositions is well known in the art. Except insofar as any conventional media or agent is incompatible with the genetically modified cells of the present invention, use of such conventional media or agent in the therapeutic compositions is contemplated. Supplementary active ingredients can also be incorporated into the compositions.

The therapeutic compositions of the present invention may be administered to an animal in need thereof. Accordingly, the present invention provides methods for inducing an immune response in an animal in need of such response, which comprise administering to an animal an immunologically effective amount of the subject genetically modified cells. The present invention also provides methods for preventing or treating a tumor in an animal, which comprise administering to an animal an anti-tumor effective amount of the subject genetically modified cells.

The term "animal" used herein encompasses all mammals, including human. Preferably, the animal of the present invention is a human subject.

The immune response induced in the animal by administering the subject genetically modified cells may include cellular immune responses mediated primarily by cytotoxic T cells, capable of killing tumor cells, as well as humoral immune responses mediated primarily by helper T cells, capable of activating B cells thus leading to antibody production. A variety of techniques may be used for analyzing the type of immune responses induced by the subject genetically modified cells, which are well described in the art; e.g., Coligan et al. *Current Protocols in Immunology*, John Wiley & Sons Inc. (1994).

The term "preventing a tumor" used herein means the occurrence of the tumor is prevented or the onset of the tumor is significantly delayed. The term "treating a tumor" used herein means that the tumor growth is significantly inhibited, which is reflected by, e.g., the tumor volume. Tumor volume may be determined by various known procedures, e.g., obtaining two dimensional measurements with a dial caliper.

When "an immunologically effective amount", "an anti-tumor effective amount", or "a tumor-inhibiting effective amount" is indicated, the precise amount of the genetically modified cells to be administered can be determined by a physician with consideration of individual differences in age, weight, tumor size, extent of infection or metastasis, and condition of the patient. It can generally be stated that a therapeutic composition comprising the subject genetically modified cells is conveniently administered in an amount of at least about $1 \times 10^3$ to about $5 \times 10^9$ cells per dose.

The administration of the subject therapeutic compositions may be carried out in any convenient manner, including by aerosol inhalation, injection, ingestion, transfusion, implantation or transplantation. Conveniently, the genetically modified cells of the present invention are administered to a patient by subcutaneous (s.c.), intraperitoneal (i.p.), intra-arterial (i.a.), or intravenous (i.v.) injection. The therapeutically acceptable carrier should be sterilized by techniques known to those skilled in the art.

The invention is further illustrated by the following specific example which is not intended in any way to limit the scope of the invention. We envision substituting TGFβ1 and TGFβ3 for TGFβ2 in the following example. Additionally, we envision substituting SCLC cells for NSCLC cells in the following example.

Example

In a clinical trial we use four human non-small cell lung cancer cell lines that have been previously established in tissue culture laboratory. We gene modify these tumor cells in the laboratory to block their TGFβ secretion. We then use the genetically engineered cells as vaccines in patients with non-small cell lung cancer. Patients are injected four times, in monthly intervals, with the gene modified vaccine cocktails that constitute the four non-self (allogeneic) TGFβ antisense gene modified tumor cells. Our rationale for using other people's tumor cells is that lung tumor cell lines belonging to different people have been shown to share common characteristics that are recognized by non-self immune systems. Treated patients are evaluated four months after they enter therapy. Patients that respond to therapy receive an additional four to twelve injections to evaluate whether their response to therapy can be amplified.

Patients are randomly assigned to one of three separate cohorts. The vaccine cocktail constitutes an equal number of each of the four irradiated TGFβ antisense gene modified NSCLC cell lines. The number of injected cells in the three cohorts is $1.25 \times 10^7$, $2.5 \times 10^7$, and $5 \times 10^7$ cells respectively.

Response, time to tumor progression, and tumor free survival are monitored in patients and compared with historical controls and patients receiving other forms of therapy. Patients are monitored and evaluated according to standard evaluation criteria of no response, stable disease, partial response and complete response. The results of this study are used to evaluate the feasibility of additional clinical trial with TGFβ antisense gene modified tumor cells alone and in combination with IL-2 (or other cytokine) gene modification.

Primary Objective

The primary objective of the clinical trial is to evaluate the ability of increasing doses of a gene-modified tumor cell vaccine to induce tumor response in patients with NSCLC.

Study Design

This study is designed to evaluate the efficacy of immunization with increasing doses of an allogeneic tumor cell vaccine in patients with NSCLC. Patients are followed for clinical response, immunogenicity and safety.

Eligible patients receive 4 monthly intradermal injections with a cell cocktail comprised of equal numbers of four irradiated allogeneic TGFβ2 antisense gene modified NSCLC cell lines. Patients are randomized to one of the three study cohorts. Patients receive $1.25 \times 10^7$, $2.5 \times 10^7$, or $5 \times 10^7$ gene modified cells respectively.

When available, tumor samples obtained from study patients at the time of clinically indicated surgery are used to establish a cell line for each patient. The patients' tumor cells are then used in precursor analyses or cytotoxicity assay monitoring of the patients immune responses to gene therapy inoculations.

Vaccine Administration

Patients receive intradermal injections of the tumor cell vaccine at months 0, 1, 2, 3 and 4. These are administered in an outpatient setting. The sites of injection are rotated between the upper and lower extremities. Patients are observed in the clinic for 2 hours following vaccination. During this observation period, vital signs are taken every 30 minutes. Patients experiencing no significant side effects from treatment are discharged 2 hours after vaccination.

Outline of Study Procedures

Patients are vaccinated according to the schedule outlined in the table below. Patients are initially treated once a month for 4 months, unless there is documented unmanageable toxicity or clinically significant disease progression requiring intervention with other anti-cancer therapies. Tumor staging (by comprehensive CT/MRI scans) is performed at baseline and at weeks 8, 16 and 28 and every 3 months thereafter. Patients have serial monitoring of immune response (humoral and T cell responses) every 4 weeks up to week 28 and every 12 weeks thereafter. Patients are monitored closely for toxicity throughout the study. In those patients demonstrating benefit from treatment, additional vaccinations, given every 4-8 weeks, are given for up to 12 additional vaccinations (total of 16 vaccinations).

Stopping Rules

Given that tumor responses from vaccination may follow a period of initial tumor progression, patients are allowed to stay on study in the face of non-clinically significant progression at week 8. At week 16, such patients must shown no further tumor progression (no more than a 25% increase at week 16 as compared to week 8). Patients who demonstrate progressive disease at week 16 (compared to week 8) are removed from study.

Overview of Monthly Treatment Schema

| Procedure | Screen | Day 1 | Day 2 | Day 8 | Day 29/1 |
|---|---|---|---|---|---|
| Informed consent | X | | | | |
| History, Exam[1] | X[2] | X | | | X |
| Phone contact | | | X | | |
| Vital signs, weight, PS | X[2] | X | | X | X |
| Adverse events | X[2] | X | | X | X |
| Concomitant medications | X[2] | X | | X | X |
| CBC with differential | X[1] | X | | X | X |
| Electrolyte panel | X[1] | X | | | X |
| Metabolism panel | X[2] | X | | | X |
| Tumor staging[2] | X[4] | | | | |
| Biopsy of inoculation site | | | | X | |
| Humoral Immunity[3] | X[2] | | | | X |
| Cellular Immunity[3] | X[2] | | | | X |
| Vaccine administration[4] | | X | | | X |

[X]: within X weeks prior to day 1
[1] once a month during treatment and once every 3 months in follow-up
[2] repeated at weeks 8, 16, 28, then every 12 weeks
[3] repeated at weeks 4, 8, 12, 16, 20, 24, 28, then every 12 week
[4] administered at weeks 1, 4, 8, 12. Continued administration possible for responding patients

DEFINITION OF PROCEDURES

| | |
|---|---|
| Phone contact: | Patients are contacted by phone by the study nurse to assess the degree of inflammation, pain, or puritis at local injection site |
| CBC with differential: | WBC, HCT, HGB, platelet count, % neutrophil, % lymphocytes, % monocytes |
| Electrolyte panel: | Sodium, potassium, chloride, carbon dioxide, BUN, creatinine, glucose |
| Metabolism panel: | Calcium, phosphorus, AST, ALT, alkaline phosphatase, bilirubin, uric acid, albumin, protein |
| Tumor staging: | Physical exam, x-rays, CT/MRI as appropriate. All staging should use the same method to assess tumor as used at baseline |
| Biopsy of inoculation site: | Punch skin biopsy performed at periphery of inflamed vaccination site or, if no inflammation, to include vaccination site |
| Humoral Immunity: | Serum anti-tumor titers |
| Cellular Immunity: | Immunophenotyping of peripheral blood B-cell and T-cell subsets (if sufficient cells are available) including CD3, CD4, CD8, CD16, CD20, and CD68. Measure PBC cytokine profile by quantitative (semi-quantitative), NK activity (nonspecific killing), LAK activity (Allo-killing). |

Inclusion Criteria
  Signed informed consent
  >18 years
  Histologically confirmed non-curable NSCLC with measurable disease and an estimated volume of 125 cc
  Performance status (ECOG)≦2
  Absolute granulocyte count 1,500/mm$^3$
  Platelet count 100,000/mm$^3$
  Total Bilirubin≦2 mg/dL
  AST and ALT≦2× Upper Limit of Normal
  Creatinine≦1.5 mg/Dl.

Exclusion Criteria
  Concurrent systemic steroids>20 mg prednisone/day
  Prior splenectomy
  Surgery, chemotherapy, radiotherapy, steroid therapy or immunotherapy <4 weeks of study entry
  Brain metastases or meningeal lymphomatosis unless treated and stable for 2 months
  Known HIV positive
  Serious non-malignant disease (e.g., congestive heart failure, or active uncontrolled bacterial, viral, or fungal infections), or other conditions which, in the opinion of the investigator would compromise protocol objectives.
  Prior malignancy (excluding nonmelanoma carcinomas of the skin) unless in remission for ≦2 years
  Treatment with an investigational drug within 30 days prior to study entry
  History of psychiatric disorder that would impede adherence to protocol
  Pregnant or nursing women or refusal to practice contraception if of reproductive potential.

Conduct of the Study

The study is conducted according to Good Clinical Practice, the Declaration of Helsinki and US 21 CFR Part 50—Protection of Human Subjects, and Part 56—Institutional Review Boards. Written, dated informed consent for the study is obtained from all patients before protocol-specified procedures are carried out. After signing, patients are given a copy of their informed consent. Approval of this study is obtained from the appropriate Institutional Review Board prior to enrolling patients on study. Consent forms are in a language fully comprehensible to the prospective patient.

Consent is documented either by the patient's dated signature or by the signature of an independent witness who records the patient's consent.

Tumor Response

Patients are evaluated by CT/MRI and physical examination. Response is reported using standard outcome measures for clinical trials (complete response (CR), partial response (PR), stable disease (SD) and progressive disease (PD)). Any response to treatment (either PR or CR) requires two confirmatory staging at least 4 weeks apart.

Complete Response

Resolution of all measurable disease for a period of at least 4 weeks.
Resolution of all evaluable disease for a period of at least 4 weeks.
No new lesions (either measurable or evaluable).

Partial Response

Decrease in the sum of the product of all measurable lesions by at least 50% for a period of at least 4 weeks.
Subjective improvement in evaluable disease for a period of at least 4 weeks.
No new lesions (either measurable or evaluable).

Stable Disease

Less than a 50% decrease AND less than a 25% increase in the sum of the products of all measurable lesions.
No new lesions (either measurable or evaluable).

Progressive Disease

Greater than a 25% increase in the sum of the products of all measurable lesions OR new lesions (either measurable or evaluable).

Evaluation of Immune Response

Humoral Immune Response Assessment

Humoral anti-tumor immune responses is evaluated by comparing the titer of pre-treatment and post-treatment sera for reactivity against the vaccinating cell lines using an enzyme-linked immunosorbent assay (ELISA). Briefly, $10^5$ target cells are immobilized on filter paper disks in a 96-well incubator chamber (V and P Enterprises, La Jolla, Calif.) and then incubated for 30 minutes with the test sera. The plates are washed and then incubated with an enzyme-conjugated anti-human Ig. The plates are again washed, the enzyme substrate is added, and the binding is quantitated by measuring the absorbance of each well on an ELISA reader.

Cellular Immune Response Assessment

Immunophenotyping

Standard immunofluorescence flow cytometry assays are performed to assess patients pre and post treatment immune effector cells profiles. Percentages of effector cell subpopulations reacting with monoclonal antibodies to T-cells (CD3, CD4, CD8), natural killer cells (CD16) and B-cells (CD20) are measured in the pre- and post-treatment peripheral blood lymphocyte population and correlated with patients responses measured by other criteria. Briefly, the Ficoll-Hypaque purified mononuclear cells are incubated with the primary antibody for 1 hour at room temperature, washed and then incubated with fluorochrome conjugated secondary antibody. The cells are washed, fixed, and the percentage of positive cells are determined with a flow cytometer. Incubations of the cells with isotype-matched control antibody instead of the primary antibody serve as negative controls.

Natural Killer (NK) Activity

NK activity is analyzed using a standard chromium release assay using the NK-sensitive cell line K562 as the target. Briefly, K562 cells are labeled by incubating them with $^{51}Cr$ for 45 minutes at 37° C. The target cells are washed extensively and then $5 \times 10^3$ K562 are incubated for 4 hours at 37° C. with pre- and post-treatment PBMC at effector cell:target cell ratios ranging from 100:1 to 3:1. The cells are then centrifuged and the amount $^{51}Cr$-release is measured using a gamma counter. The percent specific lysis is determined using the formula: (experimental cpm−background cpm)/(total cpm−background cpm)×100.

LAK Activity

LAK activity is determined by chromium release assay as described above, using the LAK-sensitive cell line DAUDI as the target.

Pre- and Post-Treatment Cytokine Profile of Lymphocytes

The cytokine profile of the patients PBMC is determined by semi-quantitative PCR assays. RNA is extracted from patients pre- and post-treatment purified mononuclear cells and used to synthesize first strand cDNA by an Invitrogen (San Diego, Calif.) cDNA cycle kit according to the manufacturer's recommendation. The first strand cDNA is then used as template in PCR assays employing different primer sets for detection of IL-2, IL-4, IL-6, IL-7, IL-10, GM-CSF, γ-INF, TNF-α, etc. To achieve quantitation PCR reactions are limited to 15-18 cycles. As an internal control and to aid in quantitation of the products known concentrations of a control RNA are added to each sample prior to initiation of cDNA synthesis. Specific primers for the control sequence are then added to the PCR reactions. Patient samples cytokine profiles are determined by quantitating patients' PCR products and comparing them with the control PCR products.

Skin Biopsy of Immunization Site

Standard hematoxylin and eosin staining and immunohistochemical methods employing monoclonal antibodies to hematopoietic cell subsets are employed to characterize the immune infiltrates observed in skin biopsies at immunization sites. Monoclonal antibodies to T-cells (CD3, CD4, CD8), natural killer cells (CD16) and B-cells (CD20) are utilized for these studies. Briefly, for the immunohistochemical studies, cryostat sections are fixed in cold acetone and then incubated with primary antibody for 1 hour at room temperature. The sections are washed and then incubated with horseradish peroxidase conjugated secondary antibody followed by staining sections with an appropriate chromagen substrate and examined by light microscopy. Incubations of sections with isotype-matched control antibody instead of the primary antibody serve as negative controls.

Drug Information

Clinical Formulation

The vaccine is provided in frozen vials containing at least $20 \times 10^6$ cells per vial.

Pharmacists Instructions

| Undiluted material | Vial volume: | 1 ml |
|---|---|---|
| | Appearance: | Cloudy fluid |
| | Storage: | −176° C. (Liquid Nitrogen). |

-continued

| | | |
|---|---|---|
| Hazards: | Frozen vials are not considered hazardous if unbroken. Vials contain cell frozen in a mixture containing 10% dimethyl sulphoxide and 50% fetal calf serum. | |
| Handling: | Frozen vials are not considered a safety hazard if unbroken. Broken vials should be disposed of in accordance with biohazard procedures for cytotoxic drugs. | |
| Diluted material | Preparation: | Before being injected into patients, a frozen vial is thawed in a biosafety hood and washed twice with serum containing medium and four times with lactated Ringer's. The cells are then counted and adjusted to the appropriate number of cells per injection in a volume of 250-400 µl. The cell suspension is delivered in a capped 1 mL syringe. Drug concentrate: $1.25 \times 10^7$, $2.5 \times 10^7$, or $5 \times 10^7$ cells per injection in a volume of 250-400 µl. |
| | Diluent: | Lactated Ringer's |
| | Route of administration: | Intradermal injection |
| | Storage | Frozen, unopened vials are stored at –176° C. (Liquid Nitrogen). |

Data Evaluation

Statistics and Estimated Sample Size

Patients in the amount of 27-75 are enrolled. This is a two-stage study. Each of the three treatment arms initially accrues 9 patients. Should no responses be seen in the first 9 patients, then no further patients are accrued to that treatment arm. If at least 1 response is seen in the first 9 patients, then 16 additional patients are accrued to that treatment arm for a total of 25 patients per treatment arm.

DEFINITION OF EVALUABLE PATIENTS

Patients are considered evaluable for tumor response if they have completed at least 2 vaccinations and have undergone the tumor restaging at week 8.

Patients are considered evaluable for immune response if they have had at least 1 vaccination and have had immune analysis at week 4.

Patients are eligible for toxicity following a single vaccination.

Reporting of Outcomes

Response rates are reported using descriptive statistics and report rates of CR, PR, SD, and PD in those patient determined to be evaluable. Time to progression following initial therapy is determined for those patients experiencing either a CR or PR.

Secondary endpoints include immune response, duration of response, and safety. These rates are also reported using descriptive statistics. Safety is reported as percent of patient experiencing a given adverse event. Mean time to progression for the responding population is reported using Kaplan-Meier statistics.

Unmodified NSCLC Cell Lines

Seven of the eight NSCLC lines used in the production of this vaccine are established cell lines that are purchased from American Tissue Cell Culture (ATCC). The human squamous NSCLC cell line, Rh-2, was established from a surgical resection specimen in the lab of Dr. Steven Dubinett at UCLA in 1994, and is publicly available per Lee et al. 1994 *J. Immunology* 152: 3222; Huang et al. 1995 *Cancer Research* 55: 3847; Huang et al. 1996 *J. Immunology* 157: 5512; and Huang et al. 1998 *Cancer Research* 58: 1208.

pCHEK/HBA2:TGFβ2 Antisense Plasmid

The pCHEK vector used to construct the human TGFβ2 antisense containing plasmid was derived from the pCEP4 vector (Invitrogen, San Diego, Calif.). It has been modified slightly to facilitate genetic subcloning. The resulting carrier vector is pCHEK. Genetic subcloning was used to insert the TGFβ2 antisense gene fragment (HBA2) into pCHEK. Aliquots of the pCHEK/HBA2 plasmid were examined by restriction enzyme analyses to ensure 1) the identity of the carrier vector into which TGFβ2 antisense was cloned and 2) the correct orientation of the TGFβ2 antisense insert.

Test limits: Complete homology with expected DNA fragment sizes after a series of restriction digests with 14 endonucleases: ApaI, BamHI, BglII, ClaI, EcoRV, HindIII, HpaI, NotI, NruI, PstI, SalI, SacII, ScaI, and XbaI.

Results: The observed DNA fragments obtained by these restriction digests corresponded with the expected fragment sizes of pCHEK/HBA2 plasmid. In conclusion, the vector used for subcloning is correct and the TGFβ2 antisense gene fragment insert is in the correct orientation.

The expected fragments of these restriction digests are:

| | | | | | |
|---|---|---|---|---|---|
| ApaI | 4604 bp | 3309 bp | 1957 bp | 874 bp | 219 bp |
| BamHI | 10963 bp | | | | |
| BglII | 10210 bp | 753 bp | | | |
| ClaI | 10963 bp | | | | |
| EcoRV | 10963 bp | | | | |
| HindIII | 7540 bp | 2787 bp | 636 bp | | |
| HpaI | 10251 bp | 712 bp | | | |
| NotI | 10963 bp | | | | |
| NruI | 5716 bp | 5247 bp | | | |
| PstI 7 | 573 bp | 1494 bp | 1277 bp | 619 bp | |
| SalI | 8738 bp | 2225 bp | | | |
| SacII | 5347 bp | 3340 bp | 2276 bp | | |
| ScaI | 8021 bp | 1915 bp | 1027 bp | | |
| XbaI | 9579 bp | 1384 bp | | | |

TGFβ2 Antisense Insert

To further ensure the correct sequence and orientation of the TGFβ2 antisense fragment, the insert was tested by sequence analyses using an ABI-310 Genetic Analyzer (Perkin Elmer, Foster City, Calif.).

Test limits: Complete homology between plasmid insert and TGFβ2 antisense.

Results: Sequencing results obtained confirmed the presence of human TGFβ2 fragment in the pCHEK vector. These results also confirmed the correct orientation of the insert. The sequence of the human TGF 2 fragment used in construction of the pCHEK/HBA2 vector and its flanking regions in the vector are as follows. Lower case letters represent the two vector sequences that flank human TGFβ2 fragment.

tgtctggatc cggccttgcc ggcctcga (SEQ ID NO: 2)—vector sequence flanking the insert—

Base pair 5 of human TGFβ2

```
                                          (SEQ ID NO: 1)
AATTCAAGCAGGATACGTTTTCTGTTGGGCATTGACTAGATTGTTTGCA

AAAGTTTCGCATCAAAAACAACAACAACAAAACAAACAACTCTCCTTGAT

CTATACTTTGAGAATTGTTGATTTCTTTTTTTATTCTGACTTTTAAAAA

CAACTTTTTTTTCCACTTTTTAAAAAATGCACTACTGTGTGCTGAGCGC

TTTTCTGATCCTGCATCTGGTCACGGTCGCGCTCAGCCTGTCTACCTGCA

GCACACTCGATATGGACCAGTTCATGCGCAAGAGGATCGAGGCGATCCGC

GGGCAGATCCTGAGCAAGCTGAAGCTCACCAGTCCCCCAGAAGACTATCC

TGAGCCCGAGGAAGTCCCCCCGGAGGTGATTTCCATCTACAACAGCACCA

GGGACTTGCTCCAGGAGAAGGCGAGCCGGAGGGCGGCCGCCTGCGAGCGC

GAGAGGAGCGACGAAGAGTACTACGCCAAGGAGGTTTACAAAATAGACAT

GCCGCCCTTCTTCCCCTCCGAAACTGTCTGCCCAGTTGTTACAACACCCT

CTGGCTCAGTGGGCAGCTTGTGCTCCAGACAGTCCCAGGTGCTCTGTGGG

TACCTTGATGCCATCCCGCCCACTTTCTACAGACCCTACTTCAGAATTGT

TCGATTTGACGTCTCAGCAATGGAAGAATGCTTCCAATTTGGTGAAAG

CAGAGTTCAGAGTCTTTCGTTTGCAGAACCCAAAAGCCAGAGTGCCTGAA

CAACGGATTGAGCTATATCAGATTCTCAAGTCCAAAGATTTAACATCTCC

AACCCAGCGCTACATCGACAGCAAAGTTGTGAAAACAAGAGCAGAAGGCG
```

AATGGCTCTCCTTCGATGTAACTGATGCTGTTCATGAATGGCTTCACCAT

AAAGACAGGAACCTGGGATTTAAAATA

Base pair 935 of human TGFβ2.—agcttgct agcagctggt acccagct (SEQ ID NO: 3)—vector sequence flanking the insert Gene-Modified NSCLC Cell Lines Following transfection, clones of each gene-modified cell line were tested for the presence of pCHEK/HBA2 vector by PCR. Only those clones testing positive for pCHEKlHBA2 were chosen for further analysis.

Results: Colonies from seven of the eight cell lines tested were positive for TGFβ2 antisense transfection. The cell line NCI-H-292 was negative.

TGFβ2 Downregulation

Following transfection, clones of each gene-modified cell line were tested for TGFβ2 downregulation by Enzyme Linked Immunosorbent Assay (ELISA) and compared to unmodified parental cell lines. Briefly, serum free supernatant of TGFβ2 antisense gene modified cells cultures was collected after 24 hr and assayed in triplicate for TGFβ2 secretion levels employing an ELISA kit (Genzyme, Cambridge, Mass.). The human TGFβ2 was captured by an anti-human TGFβ2 monoclonal antibody and quantitated by reaction with horse radish peroxidase-conjugated goat anti-human TGFβ2 antisera according to the manufacturer's recommendation. Quantitation was achieved by developing the enzymatic reaction with a chromagen substrate and reading the optical density on a micro-ELISA plate reader. A standard TGFβ2 curve presenting known concentrations of TGFβ2 permitted quantitation of TGFβ2 secretion by the TGFβ2 antisense gene modified cells.

Test limits for unmodified tumor cells: Secretion of at least 200 pg TGFβ2/$10^6$ cells/24 hr.

Test limits for gene-modified tumor cell lines for vaccine: Lowering of TGFβ2 production by at least 35% relative to unmodified parental cells. This test limit has been demonstrated to enhance immunogenicity of tumor cells in vaccination regimens, per Lee et al. 1994 *J. Immunology* 152: 3222.

Approximately 3-4 days prior to initiation of therapy, aliquots of each gene-modified cell line are re-tested for TGFβ2 inhibition. The same test limits apply.

| Cell Line | Lung Carcinoma | Unmodified TGFβ2 Levels (ng/$10^6$ cell/24 hr) | Gene modified TGFβ2 Levels (ng/$10^6$ cell/24 hr) | % TGFβ2 Down regulation |
|---|---|---|---|---|
| NCI-H-292 | Mucoepidermoid | ND | ND | ND |
| NCI-H-460 | Large cell | 0.67 | 0.12 | 82% |
| NCI-H-520 | Squamous | 2.27 | 1.43 | 37% |
| NCI-H-596 | Adenosquamous | 1.5 | 2.6 | −73% |
| NCI-H-661 | Large cell | 13.1 | 12.96 | 1% |
| SK-LU-1 | Adenocarcinoma | 3.58 | 1.36 | 62% |
| SK-MES-1 | Squamous | 1.2 | 1.36 | −13% |
| Rh-2 | Squamous | 1.16 | 0.1 | 91% |

The 4 cell lines selected were: NCI-H-460, NCI-H-520, SK-LU-1 and Rh-2. In our hands, TGFβ2 antisense gene modifications resulted in 37-91% blockage of intrinsic TGFβ2 expression in tumor cells. Suppression of TGFβ2 expression in these cells has been stable for period of six to nine months in culture.

Cell Density

Prior to patient vaccination cell density is assessed for each cell line. An aliquot of each cell line to be used is counted using a hemocytometer to ascertain cell density. Equal numbers of each gene-modified cell line is admixed for the three doses to be investigated in this study ($1.25\times10^7$, $2.5\times10^7$ and $5\times10^7$ total cells respectively).

Cell Viability

Prior to patient vaccination cell viability is also assessed for each cell line. The viability of cells employed for immunization is evaluated by trypan blue exclusion methods. Trypan blue dye is a measure of plasma membrane integrity. Viable cells maintain plasma membrane integrity and therefore exclude the dye. Dead cells lose membrane integrity and allow uptake of the dye thus appearing blue. An aliquot of each cell line is tested and cells counted in a hemocytometer. The percentage of viable "non-blue" cells is determined.

Test Limits: The viability of the TGFβ2 antisense gene modified tumor cells used for therapy must be greater than 50%.

Clonogenicity

To ensure safety, all gene-modified tumor cell lines to be used in patient vaccinations must be irradiated prior to injection. This is to prevent tumor cell growth and replication. Cells are irradiated prior to use with a dose of 10,000 cGy. The selection of this radiation dose is based on discussions with Dr. Herman Suit, Chief of Radiation Oncology at Massachusetts General Hospital. This was the lowest radiation dose sufficient to render the tumor cells incapable of proliferation and tumor formation. It is our desire to utilize the lowest possible radiation dose for the transfected cells to optimize the level and duration of TGFβ2 antisense transcription. In addition, we have tested this irradiation dose in our laboratory on cultured tumor cells of different histologic origins, including human NSCLC, gliomas, colon cancer, and pancreatic carcinoma cell lines and demonstrated that it is capable of completely arresting colony formation by cultured tumor cells of different histologic origins.

Samples of unmodified and gene modified human NSCLC cell lines were irradiated with 10,000 centi-Grays. The irradiated cells were then cultured in T-225 flasks and observed for colony formation. A colony was defined as a cluster of 16 growing cells. As presented in the table below, colonies did not form in the irradiated cultures during a four-six week observation period. In contrast, all the non-irradiated control cultures became confluent after 10-14 days. Cell death occurred approximately two weeks after initiation of the irradiated cultures.

| Effect of radiation on primary NSCLC cell cultures | | |
|---|---|---|
| Tumor cells | Radiation Dose (Gys) | # Colonies at 5 weeks |
| Control cultures | None | Confluent after 10-14 days |
| NCI-H-292 | 10,000 | None |
| NCI-H-460 | 10,000 | None |
| NCI-H-520 | 10,000 | None |
| NCI-H-596 | 10,000 | None |
| NCI-H-661 | 10,000 | None |
| SK-Lu 1 | 10,000 | None |
| SK-MES-1 | 10,000 | None |
| Rh-2 | 10,000 | None |

Prior to vaccination, an aliquot of each gene-modified cell line is thawed and tested for colony formation during a four to six week culturing period before each lot is deemed safe for patient injection.

Test Limits: No colony formation.

Sterility of Cell Lines

Sterility testing was performed for each unmodified cell line by ATCC, the manufacturer of the cells.

In addition, aliquots of each line were sent to Molecular Diagnostics Associates to assay for the presence of the following viral agents:

| | | |
|---|---|---|
| HIV 1 & 2 | HBV | CMV |
| HH-6 | HCV | HTLV |
| EBV | | Adventitious viruses |

Results: All eight unmodified master cell lines were found to be negative for the presence of bacteria, fungi and viruses.

During in vitro growth and manipulations each cell line was routinely tested for bacterial, fungal, and mycoplasma infection. To avoid contamination with other cells, cultures were processed individually at all points during laboratory manipulations. Finally, on the day of therapy, a sample of the inoculum is retested by a gram stain. Only cells that pass all sterility testing are used for therapy.

Test limits are: No bacteria, mycoplasma or fungal infections.

Clinical Grade pCHEK/HBA2 Plasmid

Following preliminary characterization of pCHEK/HBA2 plasmid, DNA stocks were prepared from bacterial cultures by the alkaline lysis method of Birnboim and Doly as optimized by Qiagen Corporation (Birnboim and Doly, 1979), and purified on Qiagen EndoFree Giga prep columns. All steps were carried out under sterile conditions using ART barrier tips in the biosafety flow hood. An aliquot of the plasmid DNA was removed and tested for sterility. Briefly 20 μl of plasmid DNA was used to inoculate four culture tubes each containing 5 ml of antibiotic free LB. The cultures were incubated for five days at 37° C.

Test Limits: No bacteria growth.

Results: No colonies were observed confirming the sterility of the prepared clinical grade DNA.

Brief General Description of Manufacturing and Packaging Procedures

Eight established NSCLC cell lines were purchased from American Tissue Cell Culture (ATCC) or otherwise and were expanded and frozen as unmodified Master Cell Banks (un-MCB). Each line was tested for sterility (bacterial and viral contaminants), clonogenicity and TGFβ2 expression. Aliquots of each line were thawed and transfected with pCHEK/HBA2, a vector containing the TGFβ2 antisense transgene, using standard techniques. Gene-modified cell lines were expanded in culture, under hygromycin selection, to grow sufficient numbers for therapeutic applications and testing. Expanded cell lines were then assayed for down-regulation of TGFβ2 expression and sterility. Four NSCLC cell lines which demonstrated successful downregulation of TGFβ2 expression and sterility were identified: NCI-H-460, NCI-H-520, SK-LU-1 and Rh-2. These cell lines were frozen in aliquots as (1) gene-modified Master Cell Banks (gmWCB) and (2) gene-modified Working Cell Banks (gmWCB) and stored in liquid nitrogen. Before use, aliquots of these four cell lines are thawed from the gmWCB, irradiated with 10,000 Gy and re-tested for sterility, clonogenicity and TGFβ2 downregulation. Only cell lots passing all test limits are acceptable for vaccine preparation. On the day of injection, sufficient cells from each of the acceptable gmWCB lots are then thawed, irradiated and admixed in equal numbers. Before patient vaccination, a sample of the inoculum is tested for bacterial contamination. If no contamination is detected, vaccination can proceed.

Tissue Procurement

The following eight established NSCLC cell lines were obtained from American Type Culture Collection (ATCC) or otherwise, expanded in culture and frozen as the unmodified Master Cell Banks (Total 8 unMCB). Cell lines were cultured in IMDM supplemented with 10% FBS, 25 mM Hepes, 2 mM L-glutamine, 1 mM sodium pyruvate, 2.5 µg/ml fungizone, 50 µg/ml gentamycin sulphate, $10^{-4}$ M α-thio-glycerol and non-essential amino acids. Each cell line was frozen as one lot containing 100 vials at >$10^6$ cells/vial. Each line was tested for sterility and TGF 2 expression. The following cell lines were used:

NCI-H-292
NCI-H-460
NCI-H-520
NCI-H-596
NCI-H-661
SK-LU-1
SK-MES-1
Rh-2

Construction of Human TGFβ2 Antisense Expression Plasmid

PCHEKIHBA2 Plasmid Description

The pCHEK vector used to construct the human TGFβ2 antisense expression plasmid (pCHEK/HBA2) was derived from the pCEP4 vector (Invitrogen, San Diego, Calif.) to facilitate gene modification of cancer cells and to eliminate safety concerns. The pCHEK vector is identical to the pCEP4 vector in all regions except the following:

Kanamycin resistance, instead of the ampicillin resistance is incorporated into the pCHEK vector.

In the pCHEK vector, a DNA cassette unit consisting of the SV-40 early promoter followed by an intron drives the expression of the hygromycin resistance gene. Incorporation of the SV-40 promoter/intron unit is to increase expression of the hygromycin resistance gene to facilitate selection of gene modified cells in culture.

The pCHEK/HBA2 plasmid utilizes a CMV promoter to drive the expression of a 930 base pair human TGFβ2 fragment in antisense orientation. The TGFβ2 antisense fragment consists of bases 6-935 of the 5' end of the human TGFβ2 cDNA molecule that was ligated in reverse orientation adjacent to and under the control of the CMV promoter. The pCHEK vector also contains the hygromycin resistance gene driven by the SV-40 early promoter, the Epstein-Barr virus origin of replication, and the gene for the Epstein-Barr virus nuclear associated protein 1 (EBNA-1). Additionally, the vector contains the ColE1 origin and kanamycin resistance genes for selection of bacteria containing vector during DNA manufacture.

pCHEK VECTOR DOMAINS

| Domain | Fragment containing the domain |
|---|---|
| SV-40 Poly A signal | 1-405 |
| Multiple cloning site | 406-463 |
| CMV promoter | 467-1311 |
| TK poly A signal | 1312-1843 |
| Hygromycin | 1844-2899 |
| Intron | 2900-3233 |
| SV-40 early promoter | 3234-3602 |
| ColE1 Origin & Kanamycin resistance | 3603-5188 |
| EBNA-1 | 5189-7789 |
| Epstein Barr origin of replication (OriP) | 7790-1046 |

Subcloning TGFβ2 Antisense into pCHEK Vector

TGFβ2 Isolation

To construct the pCHEK/HBA2 plasmid we first constructed pCEP4/HBA2, a shuttle vector. Briefly, the plasmid pPC21 (publicly available from Dr. Purchio) containing the human TGFβ2 gene was digested to completion with EcoRI. The EcoRI ends were blunt ended by adjusting the reaction conditions to 250 µM each dATP, dCTP, dGTP, and dTTP and adding 3 units Klenow enzyme to initiate the reaction. The reaction was allowed to proceed for 30 minutes at 37° C. The reaction volume was then adjusted to 100 µl with TE and phenol/chloroform extracted. The DNA was isopropanol precipitated and rinsed with 70% ethanol. The 930 base pair TGFβ2 fragment (HBA2) was released from the vector by Hind III digestion. Following electrophoresis in a 1% agarose gel, a gel slice containing the 930 bp TGFβ2 fragment was excised and the DNA fragment extracted by routine oxidized silica (glass powder) method. The TGFβ2 DNA was then ready to be ligated into the pCEP4 vector.

pCEP4/HBA2 Shuttle Vector Construction

The pCEP4 vector was prepared by digestion with XhoI restriction enzyme, and blunt ended by Klenow reaction as described above. Following phenol/chloroform extraction and ethanol precipitation, the vector was digested with Hind III and purified by agarose gel electrophoresis/glass powder method as described above.

The 930 base pair human TGFβ32 fragment was directionally subcloned into the pCEP4 vector in antisense orientation. Following transformation of E. coli, pCEP4/HBA2 DNA was prepared from several ampicillin resistant transformed bacterial colonies. The isolated DNA from these colonies was characterized by restriction enzyme analysis and one clone designated as pCEP4/HBA2 was selected and used for construction of the clinical plasmid pCHEK/HBA2.

pCHEK/HBA2 Expression Plasmid Construction

Briefly, the pCEP4/HBA2 DNA was digested with restriction enzymes KpnI and BamHI and the 930 bp TGFβ2 antisense insert fragment was purified by agarose gel electrophoresis. The insert was then ligated into the KpnI and BamHI digested pCHEK vector, and used to transform bacteria. Following kanamycin selection of overnight culture, pCHEK/HBA2 DNA was isolated from several clones and characterized by restriction enzyme analyses to ensure correct identity. To further ensure the correct sequence and orientation of the TGFβ2 antisense fragment, the insert was tested by sequence analyses using an ABI-310 Genetic Analyzer (Perkin Elmer, Foster City, Calif.).

Manufacturing of Clinical Grade pCHEKIHBA2 Plasmid

Following preliminary characterization, one bacterial colony containing the pCHEK/HBA2 plasmid was streaked on a Luria-Bertani (LB) agar plate containing 100 µg/ml kanamycin. Following incubation at 37° C., a single bacterial colony was used to inoculate 5 ml of LB broth containing 100 µg/ml kanamycin and grown overnight at 37° C. in a shaking bacterial incubator. This overnight culture was used to inoculate 50 ml culture of plasmid containing bacteria. The 50 ml bacterial culture was incubated overnight and used to inoculate flasks containing 2 liters of LB plus 100 µg/ml kanamycin. This was grown overnight at 37° C.

DNA was prepared from bacterial cultures by the alkaline lysis method of Birnboim and Doly as optimized by Qiagen Corporation (Birnboim and Doly, 1979), and purified on Qiagen EndoFree Giga prep columns. All steps were carried out under sterile conditions using ART barrier tips in the biosafety flow hood.

An aliquot of DNA was removed for restriction analysis and determination of DNA concentration. The plasmid DNA concentration was adjusted to one mg/ml, divided into aliquots, and stored at −70° C. for future use. An aliquot of the plasmid DNA was removed and tested for sterility.

Genetic Modification of NSCLC Tumor Cell Lines with pCHEK/HBA2 Plasmid

Four aliquots of each NSCLC cell line were removed from the appropriate unMCB and grown in culture. Cells were fed with fresh medium twice a week. On the day of gene modification cells were fed with fresh medium. Four hours later cells were trypsinized, washed with serum containing medium and subsequently PBS. Cell density was adjusted to $1-2 \times 10^7$ cells per ml in a volume of 350 µl PBS and incubated on ice for 15-20 minutes. 50 µg pCHEK/HBA2 plasmid was added. The mixture was incubated on ice for an additional 10-15 minutes. The cell suspension was then transferred to a pre-chilled cuvette and incubated on ice. After five minutes the cuvettes were placed in a square wave electroporator (Genetronics, San Diego, Calif.) and subjected to three electroporation pulses of 3000 v/cm each pulse lasting 75 µseconds. 1 ml of cold fresh media containing 50 mM Hepes was added and the mixture incubated at room temperature for 10 minutes. Cells were then plated for 2 division cycles and then selection was begun (72 hours after transfection). Fresh medium containing 25 µg hygromycin/ml was added to the cultures. The gene-modified cells were expanded in culture and frozen as gene modified Master Cell Banks (gmMCB) for a total of 4 gmMCBs per cell line. The presence of pCHEK/HBA2 plasmid in gene modified cells was ascertained by PCR. In addition, five vials (5%) from each gmMCB were submitted and used for sterility testing consisting of aerobic, anaerobic, mycoplasma, and fugal assays.

Preparation and Identification of Cell Lines for Patient Vaccination

Following genetic modification, tumor cell lines were expanded in culture to grow sufficient cells for therapeutic applications and testing. Clones from each cell line passing identity, strength and safety test limits were cryopreserved in liquid nitrogen as aliquots of gene-modified Master Cell Banks (gmMCB) and gene-modified Working Cell Banks (gmWCB). Prior to patient vaccination, aliquots from each gmWCB lot are thawed and irradiated with a dose of 10,000 cGy, a radiation dose we have demonstrated to be capable of completely arresting colony formation by cultured tumor cells of different histologic origins including these NSCLC cells. Aliquots from each lot undergo safety, strength and identity tests to ensure alteration or contamination has not occurred during cell manipulations and freezing. Lots are tested for: clonogenicity, sterility and TGFβ2 downregulation.

Cell Preparation and Testing Prior to Patient Vaccination

Prior to subcutaneous immunization, aliquots of the four chosen cell lines are placed in short term cultures. Gene-modified cells are detached from culture dishes, washed and resuspended in medium, irradiated with 10,000 cGy, washed and resuspended in lactated Ringer's solution. They are then tested for sterility and viability. Only cells passing test limits are used for patient vaccination.

LITERATURE CITED

Ashley D. M. et al. Endogenous expression of transforming growth factor β1 inhibits growth and tumorigenicity and enhances Fas-mediated apoptosis in a murine high-grade glioma model. Cancer Res 58(2): 302-309, 1998.

Ashley D. M. et al. Local production of TGF β1 inhibits cerebral edema, enhances TNF-α induced apoptosis and improves survival in a murine glioma model. J Neuroimmunol 86(1): 46-52, 1998.

Baker J. C and Harland R. M. From receptor to nucleus: the Smad pathway. Curr. Opin. Gen. Devel. 7: 467-473, 1997.

Bodmer S. et al. Transforming growth factor-beta bound to soluble derivatives of the beta amyloid precursor protein of Alzheimer's disease. Biochem. Biophys. Res. Communications 171: 890-897, 1990.

Bodmer S. et al. Immunosuppression and transforming growth factor-β in glioblastoma. Preferential production of transforming growth factor-β2. J Immunol 143(10): 3222-3229, 1989.

Border, W. A. and Rouslahti E. Transforming growth factor-β in disease: the dark side of tissue repair. J. Clin. Invest. 90:1, 1992.

Chen T. C. et al. TGF-β2 and soluble p55 TNFR modulate VCAM-1 expression in glioma cells and brain derived endothelial cells. J Neuroimmunol 73(1-2): 155-161, 1997.

Constam D. B. et al. Differential expression of Transforming Growth Factor-β1, -β2, and -β3 by glioblastoma cells, astrocytes, and microglia. J. Immunol. 148: 1404-1410, 1992.

Culver K W. et al. In vivo gene transfer with retroviral vector-producer cells for treatment of experimental brain tumors. Science 256: 1550-1552, 1992.

Dorigo O. et al. Synnergy of Transforming Growth Factor beta (TGF-β) antisense and IL-2 gene therapy in the murine ovarian teratoma (MOT) model. Gynecol Oncol 71(2): 204-210, 1998.

Dranoff G. et al. Vaccination with irradiated tumor cells engineered to secrete murine granulocyte-macrophage colony-stimulating factor stimulates potent, specific, and long-lasting anti-tumor immunity. Proc. Natl. Acad. Sci. 90: 3539-3543, 1993.

Dubinett S. M. et al. Gene therapy for lung cancer. Hematol Oncol Clin North Am. 12(3): 569-94, 1998.

Eastham J. A. et al. Transforming growth factor-beta 1: comparative immunohistochemical localization in human primary and metastatic prostate cancer. Laboratory Investigation 73(5): 628-635, 1995.

Eder I E. et al. Transforming growth factors-beta 1 and beta 2 in serum and urine from patients with bladder carcinoma. J. Urology 156(3): 953-957, 1996.

Fakhrai H. et al. Cytokine gene therapy with interleukin-2 transduced fibroblasts: effects of IL-2 on anti-tumor immunity. Human Gene Therapy 6: 591-601, 1995.

Fakhrai H. et al. Eradication of established intracranial rat glioma by Transforming Growth Factor beta antisense gene therapy. Proc. Natl. Acad. Sci. USA 93: 2909-2914, 1996.

Friedman E. et al. High levels of transforming growth factor beta 1 correlate with disease progression in human colon cancer. Cancer Epidemiology, Biomarkers and Prevention 4(5): 549-554, 1995.

Heldin C. H. et al. TGF-β signaling from cell membrane to nucleus through SMAD proteins. Nature 390: 465-471, 1997.

Hirte, H., and Clark D. A. Generation of lymphokine-activated killer cells in human ovarian carcinoma ascitic fluid: identification of Transforming Growth Factor-beta as a suppressive factor. Cancer Immuno. Immunother. 32: 296-302, 1991.

Holladay F. P. et al. Successful treatment of a malignant rat glioma with cytotoxic T lymphocytes. Neurosurgery 31: 528-533, 1992.

Holladay F. P. et al. Antitumor activity against established intracerebral gliomas exhibited by cytotoxic T lymphocytes, but not by lymphokine-activated killer cells. J. of Neurosurgery 77: 757-762, 1992.

Holladay F. P. et al. Generation of cytotoxic immune responses against a rat glioma by in vivo priming and secondary in vitro stimulation with tumor cells. Neurosurgery 30: 499-504, 1992.

Huber B. E. et al. Retroviral-mediated gene therapy for the treatment of hepatocellular carcinoma: An innovative approach for cancer therapy. Proc. Natl. Acad. Sci. 88: 8039-8043, 1991.

Jachimczak P. et al. The effect of Transforming Growth Factor-β2-specific phosphorothioate-anti-sense oligodeoxynucleotides in reversing cellular immunosuppression in malignant glioma. J. Neurosurg. 78: 944-951, 1993.

Jakowlew S. B. et al. Expression of transforming growth factor beta ligand and receptor messenger RNAs in lung cancer cell lines. Cell Growth and Differentiation 6(4): 465-476, 1995.

Jennings M. T. et al. Transforming growth factor β as a potential tumor progression factor among hyperdiploid glioblastoma cultures: evidence for the role of platelet-derived growth factor. J Neurooncol 31(3): 233-254, 1997.

Jennings M. T. et al. TGF-β1 and TGF-β2 are potential growth regulators for medulloblastomas, primitive neuroectodermal tumors, and ependymomas: evidence in support of an autocrine hypothesis. Hum Pathol 25(5): 464475, 1994.

Jennings M. T, Pietenpol J. A. The role of transforming growth factor β in glioma progression. J Neurooncol 36(2): 123-140, 1998.

Kasid A. et al. Effects of transforming growth factor beta on human lymphokine activated killer cell precursors: Autocrine inhibition of cellular proliferation and differentiation to immune killer cells. J. Immunol. 141: 690, 1988.

Kim I. Y. et al. Successful treatment of established rat prostate cancer by transforming growth factor-1 antisense transfected tumor vaccine. American Urological Association, Inc. Annual Meeting. 1997.

Kong F. M. et al. Elevated plasma transforming growth factor-beta 1 levels in breast cancer patients decrease after surgical removal of the tumor. Annals of Surgery 222(2): 155-162, 1995.

Liau L. M. et al. Prolonged survival of rats with intracranial C6 gliomas by treatment with TGF-beta antisense gene. Neurol Res 20(8): 742-747, 1998.

Massague, J. The TGF-beta family of growth and differentiation factors. Cell 49: 437, 1987. Merzak A, McCrea S, Koocheckpour S, Pilkington G J. Control of human glioma cell growth, migration and invasion in vitro by transforming growth factor-β1. Br J Cancer 70(2): 199-203, 1994.

Miller P. W. et al. Dendritic cells augment granulocyte-macrophage colony-stimulating factor (GM-CSF)/herpes simplex virus thymidine kinase-mediated gene therapy of lung cancer. Cancer Gene Ther. 5(6):380-9, 1998

Naganuma H. et al. Transforming growth factor-β inhibits interferon-gamma secretion by lymphokine-activated killer cells stimulated with tumor cells. Neurol Med Chir (Tokyo) 36(11): 789-795, 1996.

Nandan D, Reiner N. E. TGF-beta attenuates the class II transactivator and reveals an accessory pathway of IFN-gamma action. Journal of Immunology 158(3): 1095-1101, 1997.

Ram Z. et al. In situ retroviral-mediated gene transfer for the treatment of Brain tumors in rats. Cancer Research 53: 83-88, 1993.

Ramanathan R. K; Belani C. P. Chemotherapy for advanced non-small cell lung cancer: past, present, and future. Semin Oncol. 24(4):440-54, 1997

Ransohoff J. et al. Cancer of the central nervous system and pituitary. In: American Cancer Society Textbook of Clinical Oncology. Holleb A I, Fink D J, and Murphy G P, editors, pp 329-337, 1991.

Rook A. M. et al. Effects of transforming growth factor-beta on the function of natural killer cells. Depressed cytolytic activity and blunting of interferon responsiveness. J. Immunol. 136 (10): 3916-3920, 1986.

Roth J. A. et al. Gene therapy for non-small cell lung cancer: a preliminary report of a phase I trial of adenoviral p53 gene replacement. Semin Oncol. 25(3 Suppl 8):33-7, 1988.

Sobol R. E. et al. Interleukin 2 gene therapy of colorectal carcinoma with autologous irradiated tumor cells and genetically engineered fibroblasts: a Phase I study. Clin. Cancer Res. 5(9):2359-65, 1999.

Sporn M. et al. Transforming growth factor-beta: biological function and chemical structure. Science 233: 532-534, 1986.

Stiles J. D. et al. Correlation of endothelin-1 and transforming growth factor-β1 with malignancy and vascularity in human gliomas. J Neuropathol Exp Neurol 56(4): 435-439, 1997.

Swisher S. G. et al. Adenovirus-mediated p53 gene transfer in advanced non-small-cell lung cancer. J. Natl Cancer Inst. 5; 91(9):763-71, 1999

Takenoyama M. et al. Antitumor response of regional lymph node lymphocytes in human lung cancer. Cancer Immunol Immunother. 47(4):213-20, 1998.

Trojan J. et al. Loss of tumorigenicity of rat glioblastoma directed by episome-based antisense cDNA transcription of insulin-like growth factor I. Proc. Natl. Acad. Sci., 89: 4874-4878, 1992.

Trojan J. et al. Treatment and prevention of rat glioblastoma by immunogenic C6 cells expressing antisense insulin-like growth factor I RNA. Science 259: 94-96, 1993.

Tsunawaki S. et al. Deactivation of macrophages by transforming growth factor-β. Nature 334:260, 1988.

Yamada N. et al. Enhanced expression of transforming growth factor-beta and its type-I and type-II receptors in human glioblastoma. International Journal of Cancer 62(4): 386-392, 1995.

Yingling J. M. et al. Tumor suppressor Smad4 is a transforming growth factor β-inducible DNA binding protein. Mol. Cell. Biol. 17 (12): 7019-7028, 1997.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. An isolated composition for prolonging survival of a subject having a lung cancer, said composition comprising a therapeutically effective amount of genetically modified cells, wherein said modification comprises a genetic construct that produces antisense nucleic acid molecules that inhibit production of TGFβ in said cells, wherein said genetically modified cells are non-small cell lung cancer (NSCLC) cells, or small cell lung cancer (SCLC) cells, and wherein said cells are autologous or allogenic to said subject.

2. The composition of claim 1, wherein said TGFβ is TGFβ-1.

3. The composition of claim 1, wherein said TGFβ is TGFβ-2.

4. The composition of claim 1, wherein said genetically modified cells are autologous cells.

5. The composition of claim 1, wherein said genetically modified cells are allogeneic cells.

6. The composition of claim 1, wherein said genetically modified cells are mixtures of autologous and allogeneic cells.

7. The composition of claim 1, wherein said genetically modified cells further express one or more cytokines having immunostimulatory effects.

8. The composition of claim 1, wherein said antisense molecules comprise the sequence of SEQ ID NO: 1.

9. A method for prolonging survival of a subject having a lung cancer comprising the step of administering to said subject a composition comprising a therapeutically effective amount of genetically modified cells, wherein said modification comprises a genetic construct that produces antisense nucleic acid molecules that inhibit production of TGFβ in said cells, wherein said genetically modified cells non-small cell lung cancer (NSCLC) cells, or small cell lung cancer (SCLC) cells, and wherein said cells are autologous or allogenic to said subject.

10. The method of claim 9, wherein said TGFβ is TGFβ-1.

11. The method of claim 9, wherein said TGFβ is TGFβ-2.

12. The method of claim 9, wherein said genetically modified cells are autologous cells.

13. The method of claim 9, wherein said genetically modified cells are allogeneic cells.

14. The method of claim 9, wherein said genetically modified cells are mixtures of autologous and allogeneic cells.

15. The method of claim 9, wherein said genetically modified cells further express one or more cytokines having immunostimulatory effects.

16. The method of claim 9, wherein said antisense molecules comprise the sequence of SEQ ID NO: 1.

* * * * *

SEQUENCE LISTING

<160> NUMBER OF SEQ ID NOS: 3

<210> SEQ ID NO 1
<211> LENGTH: 927
<212> TYPE: DNA
<213> ORGANISM: Homo sapiens

<400> SEQUENCE: 1

```
aattcaagca ggatacgttt ttctgttggg cattgactag attgtttgca aaagtttcgc      60
atcaaaaaca acaacaacaa aacaaacaac tctccttgat ctatactttg agaattgttg     120
atttcttttt tttattctga cttttaaaaa caactttttt ttccactttt ttaaaaaatg     180
cactactgtg tgctgagcgc ttttctgatc ctgcatctgg tcacggtcgc gctcagcctg     240
tctacctgca gcacactcga tatggaccag ttcatgcgca agaggatcga ggcgatccgc     300
gggcagatcc tgagcaagct gaagctcacc agtcccccag aagactatcc tgagcccgag     360
gaagtccccc cggaggtgat ttccatctac aacagcacca gggacttgct ccaggagaag     420
gcgagccgga gggcggccgc ctgcgagcgc gagaggagcg acgaagagta ctacgccaag     480
gaggtttaca aaatagacat gccgcccttc ttcccctccg aaactgtctg cccagttgtt     540
acaacaccct ctggctcagt gggcagcttg tgctccagac agtcccaggt gctctgtggg     600
taccttgatg ccatcccgcc cactttctac agaccctact tcagaattgt tcgatttgac     660
gtctcagcaa tggagaagaa tgcttccaat ttggtgaaag cagagttcag agtctttcgt     720
ttgcagaacc caaaagccag agtgcctgaa caacggattg agctatatca gattctcaag     780
tccaaagatt taacatctcc aacccagcgc tacatcgaca gcaaagttgt gaaaacaaga     840
gcagaaggcg aatggctctc cttcgatgta actgatgctg ttcatgaatg gcttcaccat     900
aaagacagga acctgggatt taaaata                                         927
```

<210> SEQ ID NO 2
<211> LENGTH: 28
<212> TYPE: DNA
<213> ORGANISM: Artificial Sequence
<220> FEATURE:
<223> OTHER INFORMATION: vector sequence flanking the insert

<400> SEQUENCE: 2

```
tgtctggatc cggccttgcc ggcctcga                                         28
```

<210> SEQ ID NO 3
<211> LENGTH: 26
<212> TYPE: DNA
<213> ORGANISM: Artificial Sequence
<220> FEATURE:
<223> OTHER INFORMATION: vector sequence flanking the insert

<400> SEQUENCE: 3

```
agcttgctag cagctggtac ccagct                                           26
```